(12) United States Patent
Cauley et al.

(10) Patent No.: US 11,623,075 B2
(45) Date of Patent: Apr. 11, 2023

(54) BUCCAL SWAB DELIVERY SYSTEM

(71) Applicant: ANERGENT PHARMACEUTICALS, INC., Moultonborough, NH (US)

(72) Inventors: Thomas H. Cauley, Redwood City, CA (US); Edward F. Schnipper, Redwood City, CA (US); Bruce A. Cohen, Moultonborough, NH (US); Nooshin Azimi, Menlo Park, CA (US)

(73) Assignee: ANERGENT PHARMACEUTICALS, INC., Moultonborough, NH (US)

( * ) Notice: Subject to any disclaimer, the term of this patent is extended or adjusted under 35 U.S.C. 154(b) by 287 days.

(21) Appl. No.: 16/886,007

(22) Filed: May 28, 2020

(65) Prior Publication Data
US 2020/0376241 A1 Dec. 3, 2020

Related U.S. Application Data

(60) Provisional application No. 62/853,544, filed on May 28, 2019.

(51) Int. Cl.
| | |
|---|---|
| *A61M 31/00* | (2006.01) |
| *A61K 31/485* | (2006.01) |
| *A61K 9/00* | (2006.01) |
| A61C 13/15 | (2006.01) |
| A61D 1/02 | (2006.01) |

(52) U.S. Cl.
CPC .............. *A61M 31/00* (2013.01); *A61K 9/006* (2013.01); *A61K 31/485* (2013.01); *A61C 19/003* (2013.01); *A61D 1/025* (2013.01); *A61M 2202/30* (2013.01); *A61M 2210/0625* (2013.01)

(58) Field of Classification Search
CPC .............. A61M 31/00; A61M 2202/30; A61M 2210/0625; A61M 37/0069; A61M 31/002; A61K 9/006; A61K 31/485; A61C 19/003; A61D 1/025
See application file for complete search history.

(56) References Cited

U.S. PATENT DOCUMENTS

| | | | | |
|---|---|---|---|---|
| 5,558,874 A | * | 9/1996 | Haber | A61K 9/7092 401/196 |
| 2010/0104625 A1 | * | 4/2010 | Putnam | A61K 9/1694 514/180 |

* cited by examiner

*Primary Examiner* — Amber R Stiles
(74) *Attorney, Agent, or Firm* — Kilpatrick Townsend & Stockton LLP

(57) ABSTRACT

Described herein is a drug product delivery device and method of delivering a drug on a swab. The drug product delivery device may include an applicator platform housed within a rigid housing. The applicator platform may be in the form of a plunger. The foil drug reservoir cap creates a fluid storage chamber disposed between the foil drug reservoir cap and the plunger. A series of fluidic channels carry fluid from the fluid storage chamber to an applicator. A frangible seal is attached to the plunger between the fluid storage chamber and the applicator. The frangible seal blocks a fluid from moving from the fluid storage chamber into the series of fluidic channels. Actuation of the plunger causes the frangible seal to be ruptured, which causes the fluid to exit the fluid storage chamber and enter into the fluidic channels. The fluidic channels carry the fluid to the applicator.

20 Claims, 11 Drawing Sheets

BUCCAL SWAB DELIVERY SYSTEM

CROSS-REFERENCE TO RELATED APPLICATION

This application claims the benefit of U.S. Provisional Application No. 62/853,544, filed May 28, 2019, which is incorporated herein by reference in its entirety.

TECHNICAL FIELD

Described herein are a method and a device for delivering a drug to a patient via a buccal swab.

BACKGROUND

The opioid crisis afflicting the United States results in a large number of annual deaths nationwide. Since the introduction of high potency synthetic opioids such as fentanyl in the illicit drug market in recent years, the number of deaths in some states has sharply increased (see FIG. 1), leading to a national emergency.

The 63,632 drug overdose deaths in the United States in 2016 represented a 21.4% increase from 2015; two thirds of these deaths involved an opioid. From 2015 to 2016, drug overdose deaths increased in all drug categories examined. The largest increase occurred among deaths involving synthetic opioids other than methadone (synthetic opioids), which include illicitly manufactured fentanyl (IMF). Since 2013, driven largely by IMF, including fentanyl analogs, the current wave of the opioid overdose epidemic has been marked by increases in deaths involving synthetic opioids. Of the 70,237 drug overdose related deaths in 2017, 47,600 (67.8%) involved an opioid. From 2013 to 2017, drug overdose death rates increased in 35 of 50 states and DC, and significant increases in death rates involving synthetic opioids occurred in 15 of 20 states, likely driven by IMF.

The opioid overdose epidemic continues to worsen and evolve because of the continuing increase in deaths involving synthetic opioids. Intensified prevention and response measures are urgently needed to curb deaths involving prescription and illicit opioids, specifically IMF.

Drug delivery systems can help address this crisis by administering the drug to patients using different routes of administration. The buccal route of drug delivery has many advantages for systemic drug delivery. The noninvasive nature of administration, the ease, precision and convenience of dosing, the increased permeability of the non-keratinized buccal mucosa, and the mucosa's rich vasculature make this a suitable route of drug delivery for therapeutic indications needing rapid systemic absorption of life-saving drugs in life-threatening emergencies. Drugs absorbed through the buccal mucosa enter the body via the jugular vein, bypassing first-pass liver metabolism and gastric/intestinal enzyme-mediated degradation. The continuous exposure of the oral tissue to a multitude of substances and the high cellular turnover of the buccal mucosa make the buccal tissue robust and less prone to drug induced local toxicity and allergic reactions. However, the challenges of the buccal route of delivery are primarily related to overcoming the 70 micron mucus-coating barriers and the constant daily production and turnover of 750-1000 cc of saliva which causes a high clearance of drugs from the oral cavity.

Since retention time in the oral cavity is low, the average bioavailability fraction for transbuccal delivery systems is typically 10% or less. The marketplace is replete with dosage delivery forms that have attempted to address this problem including quick-dissolving tablets, wafers and films, immediate release and metered-dose sprays, oral and sublingual rapid-melt and slow-melt tablets, medicated gums and lozenges, mucoadhesive bioerodable preformed discs, controlled release intraoral delivery devices and micro/nanoparticle technology. Still, only a small fraction of drugs released from these dosage forms is absorbed by the tissues of the oral cavity. Many of these dosage delivery forms do not allow release of the drugs because they are polymer based, and cross-linking polymers can cause drug trapping.

Accordingly, improvements in the delivery of emergency medications and other medications are needed.

SUMMARY

Provided herein is a drug product delivery device. In one example, the drug product delivery device includes a plunger that may be a molded component with a cover film that forms a series of fluidic channels on a first elongated surface of the plunger. The drug product delivery device may include a foil drug reservoir cap bonded to a second elongated surface of the plunger. The foil drug reservoir cap creates a fluid storage chamber disposed between the foil drug reservoir cap and the second elongated surface of the plunger. The drug product delivery device may include a frangible seal component attached to the second elongated surface of the top of the plunger. The frangible seal component blocks a fluid from moving from a drug storage chamber into the series of fluidic channels. The drug product delivery device may include an applicator (e.g., a swab) positioned at the tip of the plunger and exposed to the series of fluidic channels. The plunger and its various components may be housed within a rigid housing. An activation of the plunger from an initial position within the housing to a secondary position within the housing causes the frangible seal to rupture. The activation of the plunger causes the fluid to exit the drug storage chamber and pass through the ruptured frangible seal into the fluidic channels and into contact with the applicator.

Other objects and advantages will be apparent from the following detailed description of non-limiting examples and drawings.

DETAILED DESCRIPTION

Described herein is a liquid swab buccal drug product delivery device 200 with broad applicability to the immediate delivery of small molecule drugs and other therapeutic agents by untrained personnel in emergency situations. In certain embodiments, described herein is a single use, one-step, buccal swab applicator platform for the systemic delivery of pharmaceutical formulations such as naloxone. The applicator platform includes various components to be described herein and fits within a rigid housing to form a simple one-step device that deposits a solution of a pharmaceutically active ingredient (e.g., naloxone) in a formulation containing a tincture of benzoin onto an applicator. The formulation is designed to optimize transbuccal delivery of the pharmaceutically active ingredient (e.g., naloxone) resulting in very rapid systemic blood levels. The application involves rubbing the applicator on the inside cheek of the patient. The term "applicator," as used herein, refers to swab or any other tool including an applicator and a handle. The applicator can be in any form capable of containing or absorbing a drug or solution (e.g., cotton, foam, and the like).

Figure 1:
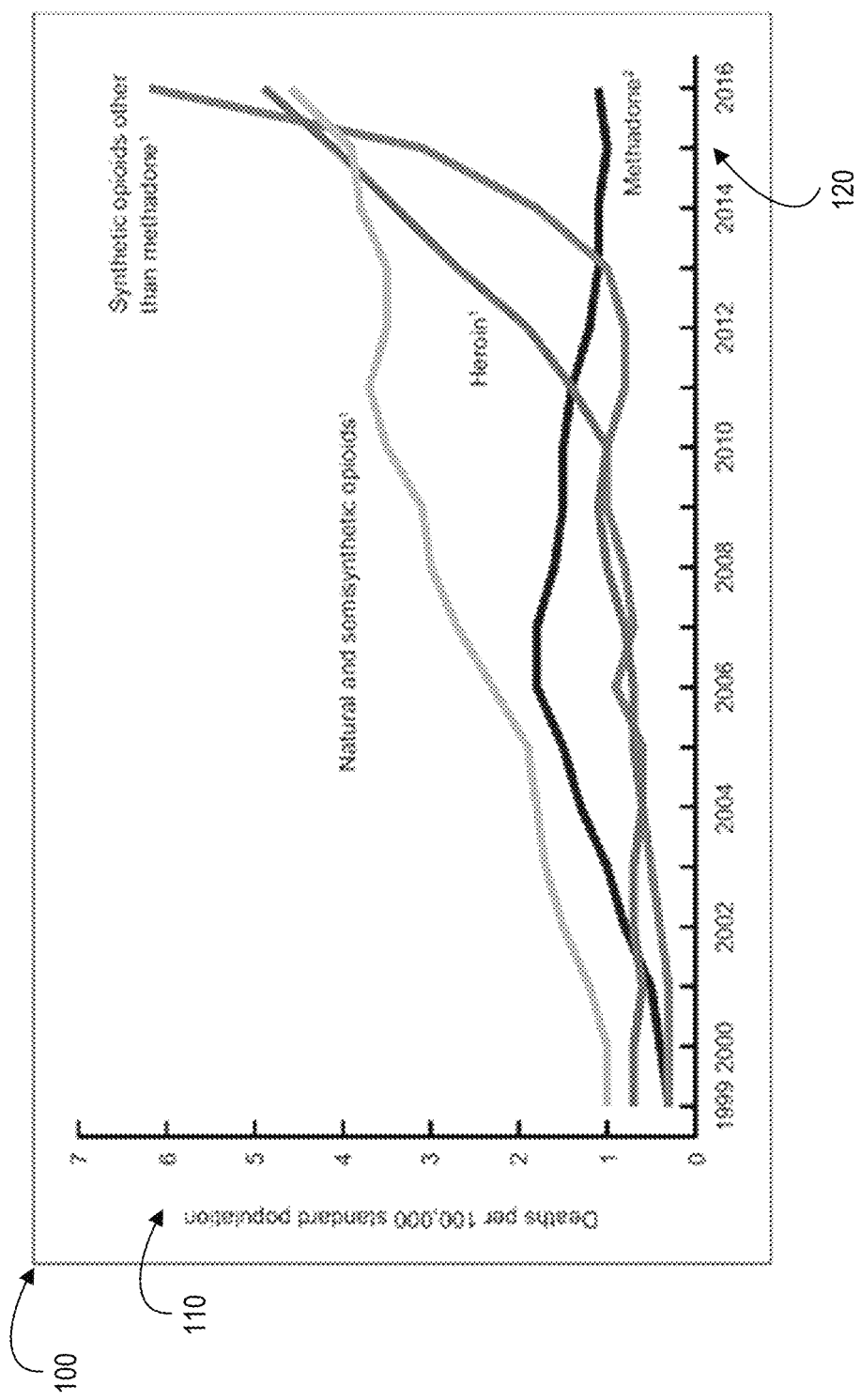
FIG. 1 is a graph depicting statistics of deaths caused by high potency opioids, according to some aspects of the present disclosure.

FIG. 1 is a graph depicting statistics of deaths caused by high potency opioids, according to some aspects of the present disclosure. In one example, the graph 100 illustrates a death rate 110 for a time period 120. As illustrated by FIG. 1, the death rate per 100,000 population for high potency opioids has seen significant increases over each successive time period 120 with the exception of methadone. In particular, the rate of increase for synthetic opioids other than methadone has outpaced the increase of all others in the most recent time periods 120 (e.g., 2013-2016). The drug product delivery device 200 described herein provides very rapid system blood levels of a pharmaceutically active ingredient to counter the impacts of high potency opioids and reduce the rate of deaths over subsequent time periods.

Figure 2:
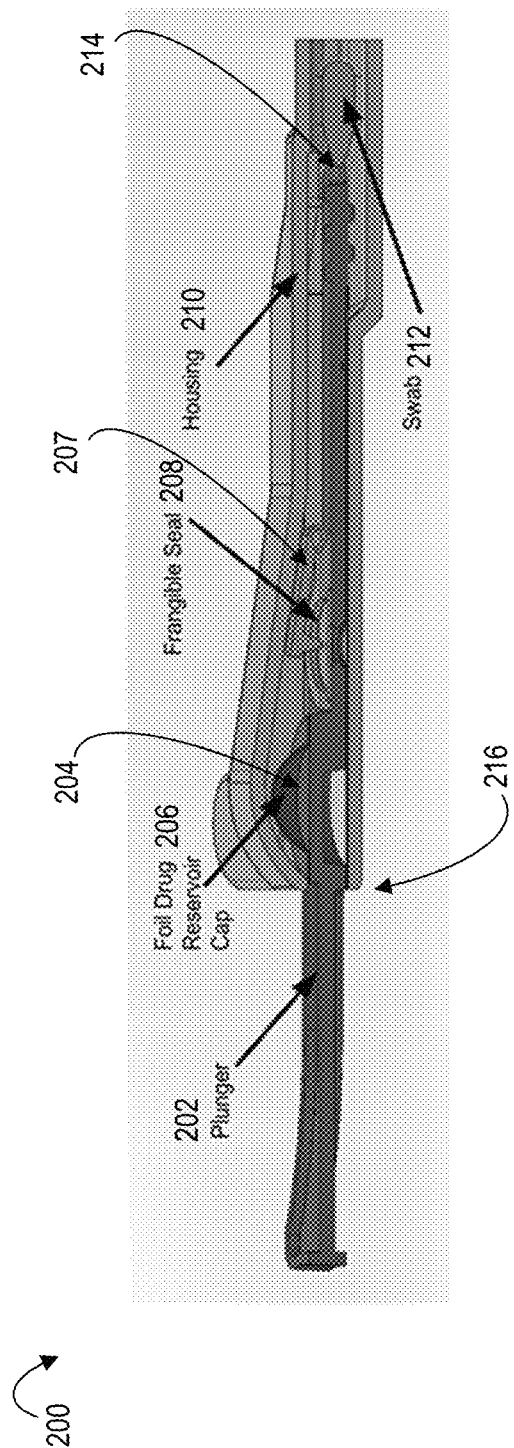
FIG. 2 illustrates a cross-sectional view of the drug product delivery device as described herein in an initial position, according to some aspects of the present disclosure.

FIG. 2 illustrates the drug product delivery device 200 as described herein, according to some aspects of the present disclosure. For example, the drug product delivery device 200 includes an applicator platform having multiple components. According to embodiments described herein, the applicator platform is provided in the form of and can be operated as a plunger 202. The plunger 202 includes a foil drug reservoir cap 206, a frangible seal 208, a housing 210, and a swab 212. The drug product delivery device 200 may be used for emergency treatments, such as treatments of known or suspected opioid overdose, as manifested by respiratory and/or central nervous system depression. The drug product delivery device 200 uses the swab 212 for the immediate administration as emergency therapy. In an example, the plunger 202 may be a molded polypropylene component with a laser welded clear cover film that forms a series of fluidic channels. The series of fluidic channels (see FIG. 3) directs the fluid from the drug reservoir to the base of the swab for delivery. The fluidic channels may be arranged to optimize flow rate to the swab 212. In some embodiments the plunger 202 may be a separate component attached to the applicator platform.

The foil drug reservoir cap 206 contains a solution of the pharmaceutical formulation in the device 200. In one example, foil drug reservoir cap 206 may be a formed foil dome with a polypropylene liner or a liner made of a similar material that is bonded to the plunger. The foil drug reservoir cap 206 may thus be in the form of a blister with its underside separated from the plunger 202 to form a chamber 204 between the foil drug reservoir cap 206 and the plunger 202. This chamber 204 forms the drug reservoir for containing the pharmaceutically active ingredient or, in some embodiments, a carrier fluid for a pharmaceutically active ingredient. The foil drug reservoir cap 206 could be formed using other liners suitable for containing a fluid.

The drug product delivery device 200 may include a frangible seal 208 attached to the top of the plunger 202. The frangible seal 208 may be formed as an assembly that includes a thin plastic or foil seal layer held in place by a thermoplastic elastomer (TPE) gasket and a seal puncture mechanism 207. The seal puncture mechanism 207 may be constructed as an overmolded rigid polypropylene part. The seal puncture mechanism 207 can alternatively be constructed using any other material and/or method, so long as the puncture mechanism 207 is compressible or depressable onto or otherwise moveable into contact with the frangible seal 208 in a manner to puncture the frangible seal 208. In some cases, the seal puncture mechanism 207 includes a hinge or joint or some other means for holding a portion of the mechanism in tension away from the frangible seal 208. The portion that is held in position away from the frangible seal 208 may be the portion of the seal puncture mechanism 207 that eventually punctures the frangible seal 208. For example, the frangible seal 208 may be ruptured by the seal puncture mechanism 207 when the plunger 202 is displaced within a housing 210. In one example, the plunger 202 is depressed towards the end of the drug product delivery device 200 that includes the swab 212. In certain embodiments, during an actuation of the plunger 202, the plunger 202 moves into a more narrow portion of the housing, which compresses the seal puncture mechanism 207 and causes it to come into contact with and rupture the frangible seal 208. Rupturing the frangible seal 208 provides a flow path from the chamber 204 towards the swab 212. In some embodiments, the seal puncture mechanism 207 may be compressed by coming into contact with a protrusion formed on or attached to the inside of the housing 210 when the plunger is pushed into the housing.

In the example illustrated by FIG. 2, the drug product delivery device 200 includes a housing 210. The housing may be a rigid plastic component (i.e., a rigid plastic housing) including one or a plurality of (e.g., two or more) molded parts that are ultrasonically welded together to form a single, rigid housing. In some embodiments, the housing 210 may be molded, cast or 3D printed as a unitary structure or as a plurality of structures that are assembled to form the finished housing 210. In some cases, the swab 212 is attached to a tip 214 of the drug product delivery device 200 that is opposite the handle end 216 of the plunger 202. An example of the swab 212 may be a sterile flock swab, such as a Puritan HydraFlock sterile flock swab with a polystyrene handle. The swab 212 receives the pharmaceutically active ingredient from fluidic channels that connect the chamber 204 and the swab 212. In some examples, the swab 212 receives the pharmaceutically active ingredient when the frangible seal 208 is ruptured to allow the fluid to exit the chamber 204 and pass into the fluidic channels 210. In some aspects, the swab 212 may be displaced or extended from within the housing 210 to deliver pharmaceutically active ingredient(s) to a patient. It is to be understood that references to a swab 212 herein are by way of example only. As mentioned, any suitable applicator may be used in place of the swab 212 in other embodiments.

The plunger 202 and the housing 210 may be manufactured using injection molding, casting, 3D printing or other suitable methodologies. In one example, the frangible seal assembly may be formed by a two shot overmolding process. The foil drug reservoir cap 206 may be made with die cutting, hot wire cutting, laser cutting, or any suitable cutting method followed by forming. The drug product delivery device 200 may be assembled using laser welding, ultrasonic welding, or any combination thereof. The pharmaceutically active ingredient is filled into the chamber 204. The chamber 204 may be heat sealed closed and the plunger 202 installed into the housing 210.

The illustrated drug product delivery device 200 is shown at rest, i.e., prior to actuation of the plunger 202. In this state, the applicator is retracted into the housing 210 and the frangible seal is unbroken such that the fluid is within the chamber 204. The drug product delivery device 200 may be placed in a formed tray and sealed closed. In some cases, the seal closure may have Quick Reference Instructions (QRI) printed on the seal closure. For example, the seal closure may include a graphical representation of the device operation to maximize its effectiveness with operators that have a wide variety of training levels.

Figure 3B:
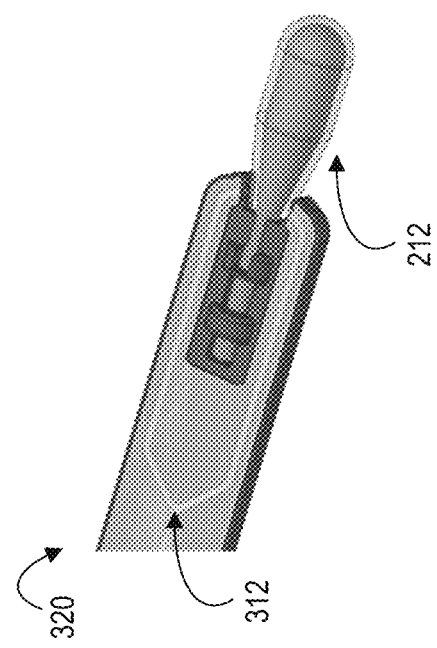
FIG. 3B illustrates another cutaway view of a portion of the exemplary drug product delivery device, according to some aspects of the present disclosure.
Figure 3A:
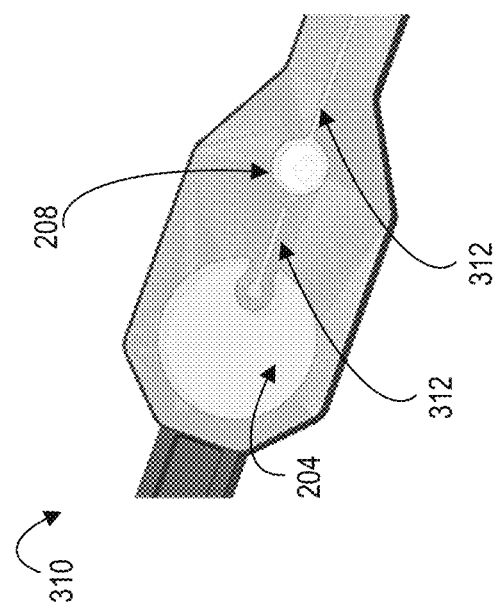
FIG. 3A illustrates a cutaway view of a portion of the exemplary drug product delivery device, according to some aspects of the present disclosure.

FIG. 3A illustrates a cutaway view of a portion 310 of the drug product delivery device 200, according to some aspects of the present disclosure. In particular, FIG. 3A shows a portion of the applicator platform, i.e., plunger 202, that includes the chamber 204, the frangible seal 208, and a fluidic channel 312 that allows fluid to pass from the chamber 204 to the frangible seal 208 and, after the frangible seal 208 is ruptured, towards the swab (not shown in FIG. 3A). The fluidic channel 312 may be formed with injection molding during the manufacture of the drug product delivery device 200. In some embodiments, fluidic channels 312 may be formed during casting or 3D printing of the applicator platform, i.e., the plunger in the illustrated example. The fluidic channel 312 may have dimensions based on a desired flow rate or based on properties of the pharmaceutically active ingredient (e.g., density, viscosity, etc.). The fluidic channel 312 receives the pharmaceutically active ingredient or other fluid from the chamber 204 and conveys the pharmaceutically active ingredient to the frangible seal 208. In an example where the drug product delivery device 200 is actuated and the frangible seal 208 is ruptured, the fluidic channel 312 provides a path for the pharmaceutically active ingredient to flow from the frangible seal 208 to the swab 212. The fluidic channel 312 path to the swab 212 is further described with regard to FIG. 3B.

FIG. 3B illustrates another cutaway view of a portion 320 of the drug product delivery device 200, according to some aspects of the present disclosure. In particular, FIG. 3B illustrates that a portion of the applicator platform, i.e., plunger 202, that includes the fluidic channel 312 and the swab 212. For instance, once the frangible seal 208 is ruptured, the region sealing the fluidic channel 312 between the chamber 204 and the swab 212 is unsealed, enabling flow through the fluidic channel 312. As illustrated by FIG. 3B, the fluidic channel 312 may include multiple fluid paths to the swab 212. The fluidic channel 312 may have any number of paths that deliver the pharmaceutically active ingredient to the swab 212.

Figure 4:
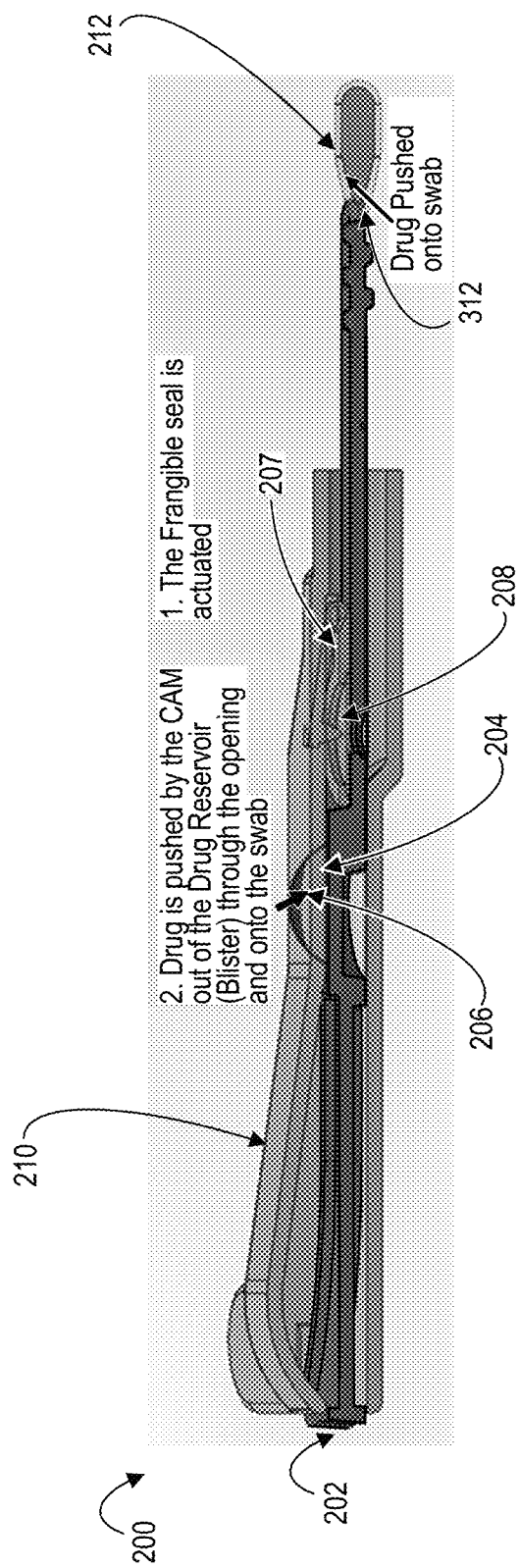
FIG. 4 illustrates the exemplary drug product delivery device in an actuated position, according to some aspects of the present disclosure.

FIG. 4 illustrates the drug product delivery device 200 in an actuated position, i.e., after actuation or displacement of the plunger 202 within the housing 210. The plunger 202 in FIG. 4 has been displaced from an initial position (i.e., the position of plunger 202 shown in FIG. 2) to an actuated or extended position shown in FIG. 4. In this position, the foil drug reservoir cap 206 is unsealed or broken to allow the fluid to exit the chamber 204 toward the frangible seal 208. In FIG. 4, the seal puncture mechanism 207 has been compressed into the frangible seal 208. The frangible seal 208 has ruptured providing a fluid path (e.g., fluidic channel 312) from the chamber 204 to the swab 212. The actuated drug product delivery device 200 provides the pharmaceutically active ingredient to the patient using the swab 212.

Figure 5:
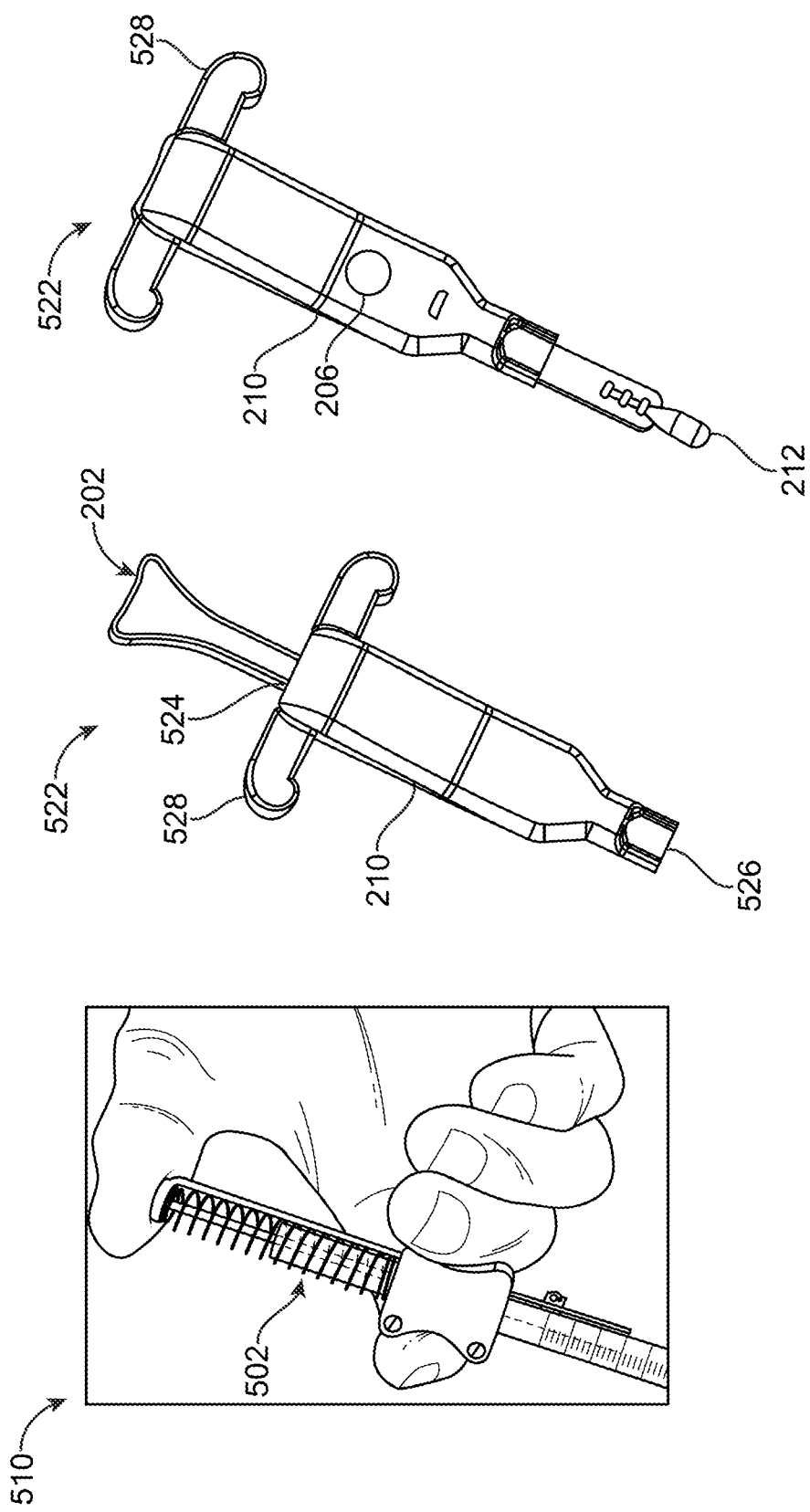
FIG. 5 depicts a user actuation orientation of an exemplary drug product delivery device, according to some aspects of the present disclosure.

FIG. 5 depicts simplified examples of an actuation orientation of an exemplary drug product delivery device 522 for administration to an unconscious person. In some examples, such as in the case of an opioid overdose, the patient may not be in a consciousness. The drug product delivery device 522 is designed to provide the pharmaceutically active ingredient regardless of the consciousness of the patient. In simplified example, a drug product delivery device 522 is illustrated in a pre-actuated position as described in additional detail with reference to FIG. 2. In pre-actuated position, the drug product delivery device 522 has the swab (not shown) retracted inside the housing 210 with the plunger in the initial position.

In another simplified example, the drug product delivery device 522 is illustrated in an actuated position as described in additional detail with reference to FIG. 4. The drug product delivery device 522 in the actuated position has the swab 212 extended from the housing 210 with the plunger 202 (not shown) in a secondary or actuated position inside the housing 210. The drug product delivery device 522 also illustrates the foil drug reservoir cap 206 that forms the chamber 204 (not shown). In the actuated position, the pharmaceutically active ingredient or other fluid flows from the chamber 204 to the swab 212 through the fluidic channels.

As shown in the simplified examples of FIG. 5, the ergonomics of the device may be configured to be similar to a feeder syringe 510—a commonly used device for the administration of fluids. The interface will be familiar and effective for device users. A handle 528 of the housing 210 is designed in combination with the handle end 216 of the plunger 202 to allow the user of the drug product delivery device 522 to administer treatment to a patient with one hand (e.g., two fingers on the handle 528 and the applicator platform, i.e., handle end 216 of the plunger 202, accessible by a thumb). A color change from the delivery of fluid to the swab 212 confirms the device has effectively delivered the fluid to the swab. In some embodiments, the Product's Instructions For Use (IFU) and Quick Reference Instructions (QRI) will indicate that a colored swab surface is required for effective device operation. The drug product delivery device 522 includes a handle opening 524. The handle opening 524 is a cavity in the housing 210 to allow the application platform (i.e., plunger 202) to be received by the housing 210. The drug product delivery device 522 may include a swab cavity 526 which contains the swab 212 within the housing 210 until actuation of the drug product delivery device 522. During actuation, the swab 212 is displaced to a second position that extends outside of the housing 210.

Figure 6:
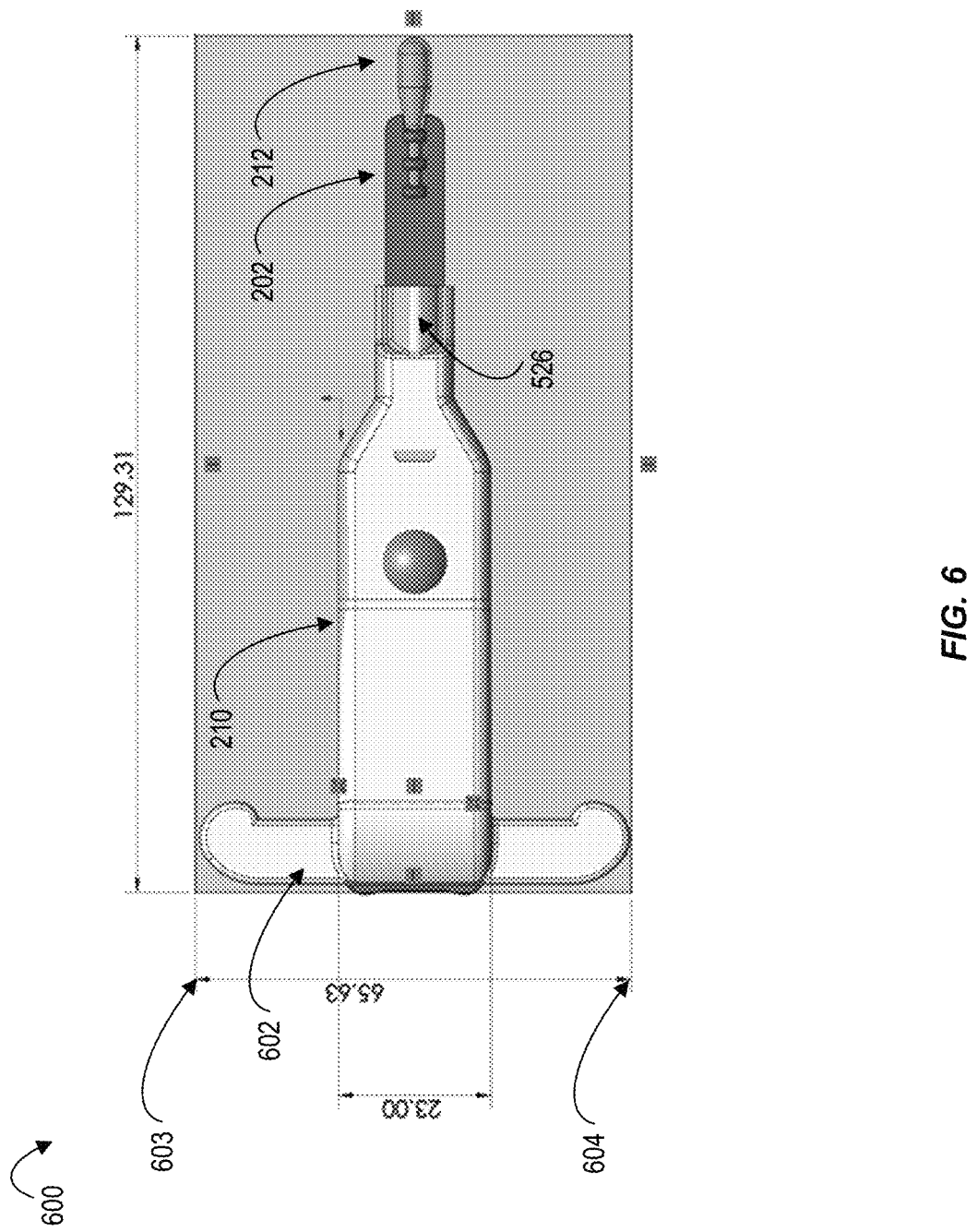
FIG. 6 illustrates the dimensions of an exemplary device, as described herein (millimeters as the unit) according to some aspects of the present disclosure.

FIG. 6 illustrates an example of a drug product delivery device 600 that includes example dimensions. For example, the drug product delivery device 600 may be substantially similar to the drug product delivery device depicted by FIG. 2 or 4. For the purposes of explanation, "length" refers to a measurement from a first end (i.e., the handle 602) to a second end (i.e., the swab), and "width" refers to a measurement from a first lateral end 603 and a second lateral end 604 of a handle component 602 of the housing 210. As can be understood with reference to FIGS. 2 and 4, the length of the drug product delivery device 600 is variable between an initial position and an actuated position. The width is fixed in both the initial position and an actuated position. The drug product delivery device 600 shown in FIG. 6 is in the actuated position with the swab 212 extended from the housing 210. In the example depicted by FIG. 6, a portion of the plunger 202 that is attached to the swab 212 extends from the swab cavity 526 at the swab end of the housing 210. In the example illustrated by FIG. 6, the drug product delivery device 600 has a length of 129.31 mm and a width of 65.63 mm. The housing 210 has a width of 23.00 mm. While FIG. 6 shows sample dimensions annotated with regard to length or width, it will be understood that such dimensions are provided by way of example only and that other suitable dimensions are possible.

Figure 7A:
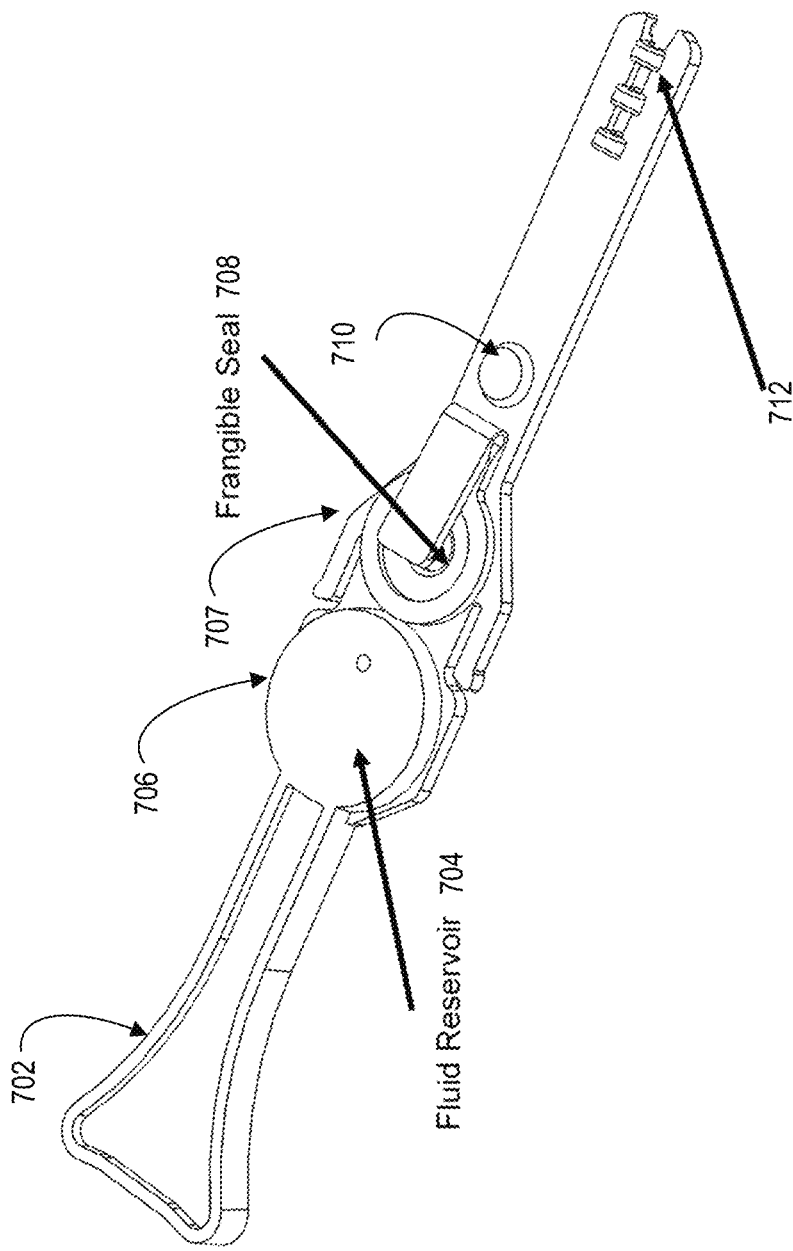
FIG. 7A shows a top side cutaway of an applicator platform, i.e., plunger 702 of a drug product delivery device, according to some aspects of the present disclosure.

FIG. 7A shows a top side cutaway of an applicator platform, i.e., plunger 702 of a drug product delivery device, according to some aspects of the present disclosure. In this example, a carrier fluid and a drug are stored in separate fluid and dry reagent (i.e., dry drug) reservoirs. For example, the separate fluid and dry reagent (i.e., dry drug) reservoirs configuration allows the drug product delivery device to be a storage and rehydration device with an integrated swab holder 712. The integrated swab holder 712 is of a size and shape suitable for holding the swab (or other type of applicator) with a tight fit to minimize movement of the swab. The plunger 702 may include two reservoirs that can be separated by frangible seals. The fluid reservoir 704, which may contain TOB and alcohol or any other viable carrier fluid is formed in a void between the foil drug reservoir cap 706 (obscured) and the plunger 702. The fluid reservoir 704 may have a single exit, such as fluidic channel 312, that leads to a dry reagent reservoir 710. The fluid reservoir 704 and the dry reagent reservoir 710 may be separated by a frangible seal 708 and a seal puncture mechanism 707. The seal puncture mechanism 707 may be depressed or compressed downward onto the frangible seal 708 and rupture frangible seal 708. In other words, the fluid reservoir 704 may be connected to the dry reagent reservoir 710 by the fluidic channel that includes a first portion between the fluid reservoir 704 and the frangible seal 708 and a second portion between the frangible seal 708 and the dry reagent reservoir 710. In some cases, the drug product delivery device 200 may include a first chamber to contain a carrier fluid and a second chamber to contain a dry (e.g., powdered, dehydrated, etc.) pharmaceutically active ingredient.

Figure 7B:
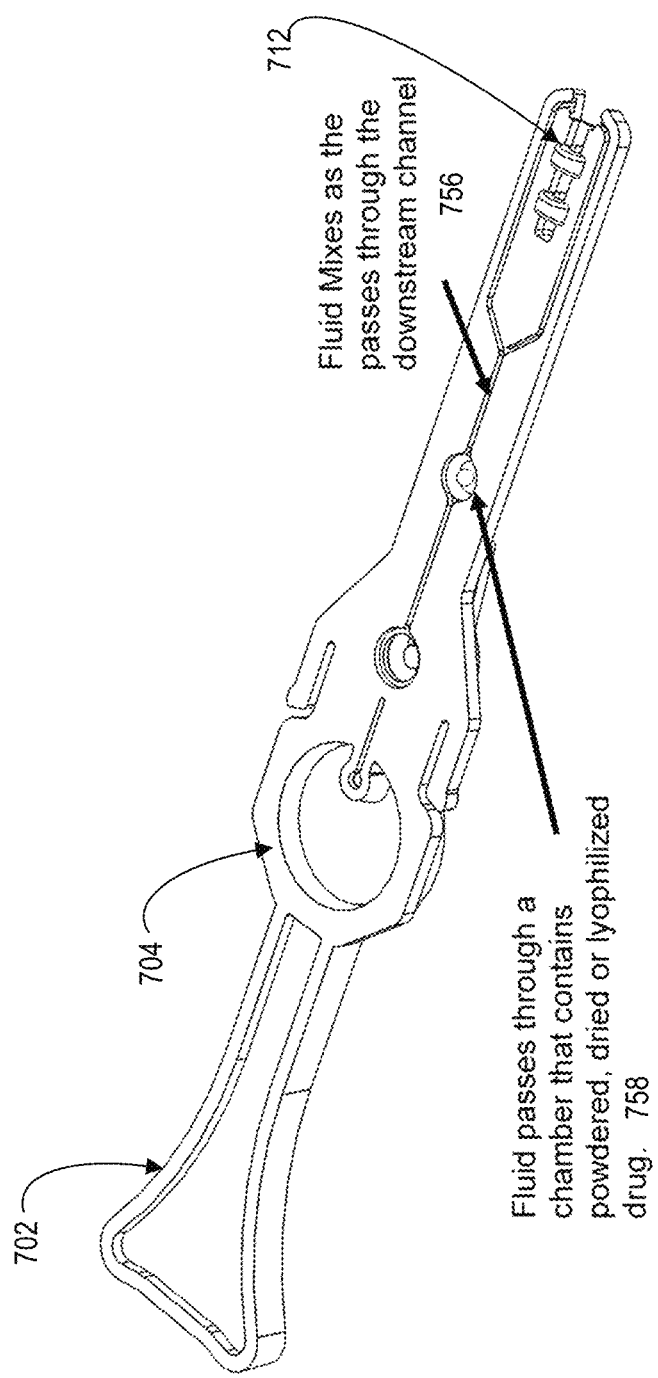
FIG. 7B illustrates an underside cutaway of the applicator platform of a drug product delivery device in which the carrier fluid and the pharmaceutically active ingredient are stored in separate fluid and dry reagent reservoirs, according to some aspects of the present disclosure.

FIG. 7B illustrates an underside cutaway of the applicator platform, i.e., plunger 702 of a drug product delivery device in which the carrier fluid and the pharmaceutically active ingredient are stored in separate fluid and dry reagent reservoirs, according to some aspects of the present disclosure. FIG. 7B more clearly illustrates the fluidic channels 756. Upon actuation of the plunger 702, the frangible seal (not shown) is ruptured and thereby creates a fluid path from the fluid reservoir 704 to the dry reagent reservoir 758. As the device is actuated further, the carrier fluid is passed through the dry reagent reservoir 758 containing the pharmaceutically active ingredient. As the carrier fluid passes through the dry reagent reservoir 758, the pharmaceutically active ingredient is rehydrated, absorbed, or dissolved. The drug product delivery device 750 may mix the pharmaceutically active ingredient to properly dissolve into the carrier fluid prior to swab positioned in integrated swab holder 712. In one example, the fluidic channel 756 can mix the pharmaceutically active ingredient by using a herringbone mixer configuration, fluid folding through meandering channels, or other microfluidic mixing geometry. The drug product delivery device 750 provides the mixed pharmaceutically active ingredient and carrier fluid to the swab positioned in integrated swab holder 712. A user of the drug product delivery device 750 can deliver the pharmaceutically active ingredient to the patient via the swab (not shown) positioned in integrated swab holder 712 contacting a portion of the patient as described herein.

The drug product delivery device 750 may include an additional frangible seal between the dry reagent reservoir 758 and the swab positioned in integrated swab holder 712. The additional frangible seal may isolate the dry reagent reservoir 758 from an environment external to the drug product delivery device 750. For example, the additional frangible seal could be used in scenarios where ambient humidity would be detrimental to rehydration performance or storage performance of the stored pharmaceutically active ingredient.

The pharmaceutically active ingredient may be stored in multiple forms including, but not limited to, dried, powdered (e.g., for chemical or small molecule drugs), or lyophollized (as in Biolyph). The pharmaceutically active ingredient may also be stored in a dissolvable film, such as one formed HydroxyPropylMethylCellulose (HPMC). HPMC is commonly used as dissolvable oral films or as fluidic gating films. The pharmaceutically active ingredient optionally can be stored for a period of time, such as one or more days, one or more weeks, one or more months, and up to a year or more. Therefore, the device described herein accommodates the storage of a drug in a volatile solution vehicle (e.g., an alcohol).

The liquid swab buccal drug product delivery device 200 described herein has broad applicability to the immediate delivery of small molecule drugs by untrained personnel in emergency situations. Various active ingredients and formulations may be delivered to a patient by the exemplary device configurations described above. Suitable active ingredients for delivery using the device described herein are provided below.

Illustrative opioid receptor antagonists suitable for buccal administration and absorption are naloxone, naltrexone and nalmefene. Illustrative opioid analgesics (i.e., narcotics) are morphine and morphine derivatives such as fentanyl, buprenorphine, carfentanil, and sulfentanil. Example non-steroidal anti-inflammatory agents (NSAIDs) include acylpropionic acid derivatives, such as ibuprofen, salicylic acid derivatives, and the like. Example anticonvulsants include iamotrigine, phenobarbital, phenytoin, and the like. Example benzodiazepines include clonazepam, diltiazem, particularly diltiazem hydrochloride (DHCl), and the like. Example triptans/serotonin agonist includes rizatriptan, zolmitriptan, and the like. Example antiemetics include ondansetron, ondansetron hydrochloride (ODAN.HCl), scopolamine, and the like. Example local anesthetics include lidocaine, particularly lidocaine hydrochloride (LHCl). Example nicotine replacement therapy agents include nicotine hydrogen tartrate (NHT).

Some more examples of drugs and other active ingredients transported through the buccal mucosa include, but are not limited to, epinephrine, flecainide, naltrexone, buprenorphine, nalbuphine, alphaprodine, pethidine, lignocaine, codeine, febuverin, cetylpyridinium chloride, tetracylcline, metronidazole, sotalol, lamotrigine, galantamine, buspirone, glyceryl trinitrate, isosorbide dinitrate, monocarboxylic acids, glucose, asenapine, nitroglycerin, captopril, nifedipine, prochlorperazine, nicotine, midazolam, acepromazine, acetaminophen, acetohexamide, acetohydroxamic acid, acetylcholine, acetylcysteine acyclovir, albendazole, alclometasone dipropionate, allopurinol, alprazolam, alprostadil, amcinoide, amantadine, amidinocillin, amikacin amiloride, aminocaproic acid, aminophylline, aminosalicylate, aminosalicylic acid, amitriptyline hydrochloride, ammonium chloride, amobarbital, amodiaquine hydrochloride, amoxapine, amoxicillin, amphetamine sulfate, amphotericin, ampicillin amprolium, acetazolamide acetyldigoxin, acetylsalicylic acid, anileridine, anthralin, antipyrine, antivenin, apomorphine, apraclonidine, ascorbic acid, aspirin, acromycin atropine, amoxycillin anipamil, azaperone azatadine maleate, azathioprine, azithromycin, aztreonam, bacampicillin, bacitracin, baclofen, barium salts, beclomethasone diproionate, belladonna extract, bendroflumethiazide, benoxinate hydrochloride, benzethonium chloride, benzocaine, benzonatate benzthiazide, benztropine mesylate, betaine, betamethasone, betaxolol, betanechol chloride, biotin, biperiden, bisacodyl, bismuth, botulism antitoxin, bromocriptine mesylate, bromodiphenhydramine hydrochloride, bumetanide, bupivacaine, busulfan butabarbital sodium, butalbital, combinations of butalbital, caffeine, beta-carotene, calcifediol, calcium carbonate, calcium citrate, calcium salts, candicidin, carbachol, carbamazepine, carbenicillin indanyl sodium, carbidopa, carbinoxamine maleate, carboprost tromethamine, carboxymethyl cellulose, carisoprodol, casanthranol, cascara, castor oil, cefaclor, cefadroxil, cefamandole nafate, cefazolin, cefixime, cefoperazone, cefotaxime, cefprozil, ceftazidime, cefuroxime axetil, cephalexin, cephradine, ceramic powder, chlorambucil, chloramphenicol, chlordiazepoxide, chloroquine phosphate, chlormadinone acetate, chlorothiazide, chlorpheniramine maleate, chloroxylenol, chlorpromazin, chlorpropamide, chlorprothixene, chlorprothixene, chlortetracycline bisulfate, chlortetracycline hydrochloride, chlorthalidone, chlorzoxazone, cholecalciferol, cholera vaccine, chromic chloride, chymotrypsin, cimetidine, cinoxazin, cinoxate, ciprofloxacin, cisplatin, clarithromycin, clavulanate potassium, clemastine fumarate, clidinium bromide, clindamycin hydrochloride, palmitate and phosphate, clioquinol, clofazimine, clofibrate, clomiphene citrate, cinnarizine, clonidine hydrochloride, clorsulon, clotrimazole, cloxacillin sodium, cyanocobalamin, cocaine, coccidioidin, cod liver oil, codeine, colchicine, colestipol, corticotropin, corisone acetate, cyclacillin, cyclizine hydrochloride, cyclobenzaprine hydrochloride, cyclophosphamide, cycloserine, cyclosporine, cyproheptadine hydrochloride, cysteine hydrochloride, danazol, dapsone, dehydrocholic acid, demeclocycline, desipramine, desoximetasone, desoxycorticosterone acetate, dexamethasone, dexchlorpheniramine maleate, dexpanthenol, dextroamphetamine, dextromethorphan, diazepam, diazoxide, dibucaine, diclofenac epolamine, dichlorphenamide, dicloxacillin sodium, dicyclomine, dienestrol, diethylpropion hydrochlorid, diethyl stilbestrol, diflunisal, digitalis, dicoumarol, digitoxin, digoxin, dihydroergotamine, dihydrostreptomycin, dihydrotachysterol, dihydroxyaluminium amino acetate, dihydroxyaluminium sodium carbonate, diltiazem hydrochloride, dimenhydrinate, dimercaprol, diphenhydramine hydrochloride, diphenoxylate hydrochloride, diphteria antitoxin, dipyridamole, disopyramide phosphate, disulfuram, dobutamine hydrochloride, docusate calcium, docusate sodium, dopamine hydrochloride, doxepin hydrochloride, doxycycline, doxycycline hyclate, doxylamine cuccinate, dronabinol, droperidol, drotaverine, dydrogesterone, dyphylline, guaifenesin, enalapril maleate, analaprilat, ephedrine, equilin, ergocalciferol, ergoloid mesylates, ergonovine maleate, ergotamine tartrate, erythrityl tetranitrate, erythromycin, estradiol, estriol, estrogene, estrone, estropipate, ethcrynic acid, ethambutol hydrochloride, ethchlorvynol, ethinyl estradiol, ethionamide, ethopropazine hydrochloride, ethotoin, ethynodiol diacetate, etidronate disodium, etoposide, eugenol, famotidine, fenoprofen, ferrous fumatate, ferrous gluconate, ferrous sulfate, flucytosine, fludrocortisone acetate, flunisolide, fluocinolone acetonide, fluocinonide, fluorescein sodium, fluorometolone, fluorouracil, fluoxymesterone, fluphenazine, flurandrenolide, flurazpam, flurbiprofen, folic acid, furazolidone, flunitrazepam, furosemide, gemfibrozil, gentamicin, gentian violet, glutarate, glutethimide, glycopyrrolate, chorionic gonadotropin, gramicidin, griseofulvin, guaifenesin, guanabenz, guanadrelsulfate, halazone, haloperidol, haloprogin, halothane, heparin calcium, hepatitis virus vaccine, hetacillin potassium, hexylresorcinol, histamine phosphate, histidine, homatropine, histoplasmin, hydralazine hydrochloride, hydrochlorothiazide, hydrocodone bitartrate, hydrocortisone, hexobarbital, hydroflumethiazide, hydromorphone hydrochloride, hydroquinone, hydroxocobalamin, hydroxyamphetamine, hydroxychloroquine sulfate, hydroxyprogesterone caproate, hydroxyurea, hydroxine hydrochloride, hydroxine pamoate, hyoscyamine, hyoscyamine sulfate, ifosfamide, imipramine, imipramide hydrochloride, indapamide, indomethacin, insulin, inulin, ocetamid, iodoquinol, iohexyl, iopamidol, ipecac, ipodate calcium, ipodate sodium, isocarboxacid, isoetharine hydrochloride, isoflurane, isoniacid, isopropamide iodine, isoproterenol hydrochloride, isosorbide dinitrate, isotretenoin, isoxsuprine hydrochloride, kanamycin sulfate, ketoprofen, ketoconazole, labetalol hydrochloride, lanolin, leucine, leucovorin calcium, levamisole hydrochloride, levocamithine, levodopa, levonorgestrel, levorphanol tartrate, levothyroxine sodium, lidocaine, lincomycin hydrochloride, lindane, liothyronine sodium, liotrix, lisinopril, lithium carbonate, loperamide hydrochloride, loracarbef, lonetil, lorazepam, lovastatin, loxapine, lysine, mafenide acetate, magaldrte, magnesium carbonate, magnesiumchloride, magnesium gluconate, magnesium oxide, other magnesium salts, malathinon, manganese salts, manganese, maprotiline hydrochloride, mazindol, measles virus vaccine, mebendazole, mebrofenin, mecamylamine hydrochloride, meclizine hydrochloride, meclocycline, meclofenamate sodium, medroxyprogesterone acetate, mefenamic acid, megestrol acetate, meglumine, melphalan, menadiol sodium diphosphate, menadione, menotropine, meperidine, mephenyloin, mephobarbital, meprednisone, meprobaamate, mercaptopurine, mesoridazine besylate, mestranol, metaproterenol sulfate, metaraminol bitartrate, methacycline hydrochloride, methadone hydrochloride, methamphetamine hydrochloride, methazolamide, methdilazine, methenamine, methicillin sodium, methimazole, methionine, methocarbamol, methotrexate, methoxsalen, methoxyflurane, methsuximide, methyclothiazide, methylbenzethonium chloride, methyldopa, methylergonovine maleate, methylphenidate hydrochloride, methylprednisolone, methyltestosterone, methysergide maleate, metoclopramide, metolazone, meoprolol tartrate, metronidazole, metyrapone, metyrosine, mexiletine hydrochloride, mexiletine hydrochloride, miconazole, minocycline hydrochloride, minoxidil, mitomycin, mitotane, molindone hydrochloride, monobenzone, morphine sulfate, mupirocin, medazepam, mefruside, methandrostenolone, methylsulfadiazine, nadolol, nafcillin, nafcillin sodium, nalidixic acid, nalorphine, nandrolone decanoate, nandrolone phenpropionate, naproxen, natamycin, neomycin, neomycin sulfate, neostimine bromide, niacin, nitrofurantoin, nalidixic acid, nitrazepam, nitrofurantoin, nitromerson, nizatidine, nonoxynol-9, norethindrone, norethindrone acetate, norfloxacin, norgestrel, nortriptyline hydrochloride, noscapine, novobiocin sodium, nystatin, opium, oxacillin sodium, oxamniquine, oxandrolone, oxazepam, oxprenolol hydrochloride, oxtriphylline, oxybenzone, oxybutynin chloride, oxycodone hydrochloride, oxycodone, oxymetazoline hydrochloride, oxymetholone, oxymorphone hydrochloride, oxyphenbutazone, oxytetracycline, padimate, panreatin, pancrelipase, papain, panthenol, papaverin hydrochloride, parachlorophenol, paramethasone acetate, paregoric, paromomycin sulfate, penicillamine, penicillin, penicillin derivatives, pentaerythritol tetranitrate, pentazocine, pentazocine hydrochloride, pentazocine salts, pentobarbital sodium, perphenazine, pertussis, phenacemide, phenazopyridine hydrochloride, phendimetrazine tartrate, phenelzine sulfate, phenmetrazine hydrochloride, phenobarbital, phenophtalein, phenoxybenzamine hydrochloride, phentermine hydrochloride, phenylalanine, phenylbutazone, phenylephrine hydrochloride, phenylpropanolamine hydrochloride, physostigmine, phytonadione, pilocarpine, pimozide, pindolol, piperazine, piroxicam plicamycin, poliovirus vaccine inactivated, polycarbophil, polymycin b sulfate, polythiazide, potassium chloride, potassium citrate, potassium cluconate, potassium iodine, potassium sodium tartrate, povidone iodine, pralidoxime chloride, pramoxine hydrochloride, pramezam, prazepam, praziquantel, prazosin hydrochloride, prazosin hydrochloride, prednisolone, prilocaine, primaquine, primidone, probenecid, probucol, procainamide hydrochlorid, procaine hydrochloride, procarbacine hydrochloride, prochlorperazine maleate, procyclidine hydrochloride, progesterone, proline, promazine, promazine hydrochloride, promazine, promethazine, promethazine hydrochloride, propafenone hydrochloride, propantheline, proparacaine hydrochloride, propoxycaine hydrochloride, propoxyphene hydrochloride, propoxyphene napsylate, propanolol hydrochloride, propyliodone, propylthiouracil, propylthiouracil, protriptyline hydrochloride, pseudoephedrine hydrochloride, pumice, pyrantel pamoate, pyrazinamide, pyrethrum extract, pyridostigmine bromide, pyridoxine hydrochloride, pyrilamine maleate, pyrimethamine, pyroxylin, pyrvinium pamoate, phenacetin, phenyloin, prednisone, uinidine gluconate, quinidine sulfate, rabies vaccine, racepinephrine ranitidine, rauwolfia serpentina, resorcinol, ribavirin, riboflavin, rifampin, ritodrine, rubella virus vaccine, saccharin, saccharin sodium, salicylamide, salsalata, secobarbital sodium, selenius acid, selenium sulfate, sennaserine, simethicone, sodium ascorbate, sodium bicarbonate, sodium fluoride, sodium gluconate, sodium iodide, sodium lactate, sodium nitrite, sodium ditroprusside, sodium salicylate, spironolactone, stannozolol, streptomycin, sucralfate, sulfacetamide, sulfadiazine, reserpine, sulfadioxine, sulfamerazine, sulfamethazine, sulfamethizole, sulfamethoxazole, sulfamethoxydiazine, sulfapyridin, sulfasalazine, sulfaperin, sulfathiazole, sulfisoxazole, sulfinpyrazone, sulindac, suprofen, stilains, tamoxifen citrate, taurine, temacepam, terbutaline sulfate, terfenadine, terpin, testolacton, testosterone, tolazamide, tolbutamide, tetracaine, tetracycline, tetrahydrocycline, theophylline, thiabendazole, thiamine hydrochloride, thiamin, thiamylal, thiethylperazine thimerosal, thioguanine, thioridazine hydrochloride, thistrepton, thiotepa, thiothixene, threonine, thyroid, ticarcillin, timolol, tioconazole, titaniumdioxide, tutanium powder, tolazamide, tolbutamide, tolmetin, tolnaftate, trazodone hydrochloride, tretinoin, triacetin, triamcinolone, triamterene, triazolam, trichorfon, trichlonnethiazide, trientine hydrochloride, trifluoperazine hydrochloride, triflupromazine, trihexyphenidyl hydrochloride, trimeprazine tartrate, trimethadione, trimethobenzamide hydrochloride, trimethoprim, trioxsalen, tripelennamine, triprolidine, tri sulfapyrimidine, tropicamide, trypsin, tryptohan, tuberculin, tyloxapol, tyropanoate sodium, tyrosine, tyrothricin, thyrothricin bethamethasone, thiotic acid, sotalol, salbutamol, norfenefrine, silymarin, dihydroergotamine, buflomedil, etofibrate, indometacin, urea, valine, valproic acid, vancomycin hydrochloride, vasopressin, verapramil, vidarabine, vinblastine, vincristine, vitamins, warfarin, yellow fever vaccine, zinc acetate, zinc carbonate, zinc chloride, zinc gluconate, beta acetyl digoxin, piroxicam, haloperidol, ISMN, amitriptylin, diclofenac, nifedipine, verapamil, pyritinol, nitrendipin, doxycycline, bromhexine, methylprdnisolone, clonidine, fenofibrate, allopurinol, pirenyepine, levothyroxin, tamoxifen, metildigoxin, o-(beta-hydroxyethyl)-rutoside, propicillin, aciclovir mononitrate, paracetamol, naftidrofuryl, pentoxifylline, propafenone, acebutolol, L-thyroxin, tramadol, bromocriptine, loperamide, ketotifen, fenoterol, cadobelisate, propanolol, enalaprilhydrogen maleate, bezafebrate, ISDN, gallopamil, xantinol nicotinate, digitoxin, flunitrazepam, bencyclane, dexapanthenol, pindolol, lorazepam, diltiazem, piracetarn, phenoxymethylpenicillin, furosemide, bromazepam, flunarizin, erythromycin, metoclopramide, acemetacin, ranitidin, biperiden, metamizole, doxepin, dipotassium chloroazepate, tetrazepam, estramustine phosphate, terbutaline, captopril, maprotiline, prazosin, atenolol, glibenclamide, cefaclor, etilfrine, cimetidine, theophylline, hydromorphone, ibuprofen, primidone, clobazam, oxaceprol, medroxyprogesterone, flecainid, pyridoxal-5-phosphate glutaminate, hymechromone, etofylline clofibrate, vincamine, cinnarizine, diazepam, ketoprofen, flupentixol, molsimine, glibornuride, dimetinden, melperone, soquinolol, dihydrocodeine, clomethiazole, clemastine, glisoxepide, kallidinogenase, oxyfedrine, baclofen, carboxymethylcysteine, thioridazine, betahistine, L-tryptophan, murtol, bromelaine, prenylamine, salazosulfapyridine, astemizol, sulpiride, benzerazide, dibenzepine, acetylsalicylic acid, miconazol, nystatin, ketoconazole, sodium picosulfate, coltyramine, gemfibrocil, rifampicin, fluocortolone, mexiletin, amoxicillin, terfenadrin, mucopolysaccharide polysulfade, triazolam, mianserin, tiaprofenic acid, amezinium metil sulfate, mefloquine, probucol, quinidine, carbamazepine, L-aspartate, penbutolol, piretanide, aescin amitriptyline, cyproterone, sodium valproinate, mebeverine, bisacodyl, 5-aminosalicylic acid, dihydralazine, magaldrate, phenprocoumon, amantadine, naproxen, carteolol, famotidine, methyldopa, auranofine, estriol, nadolol, levomepromazine, doxorubicin, medofenoxate, azathioprine, flutamide, norfloxacin, fendiline, prajmalium bitartrate, lipid derivatives of phosphonatides, amphiphilic polymers, adenosine derivatives, sulfated tannins, monoclonal antibodies, and metal complexes of water soluble texathyrin.

Additional drugs are contemplated such that this list is not intended to be exhaustive or comprehensive.

Hormones suitable for buccal absorption are the insulins (e.g., human insulin, bovine insulin, porcine insulin, and biosynthetic human insulin including Humulin®), somatostatin, vasopressin, calcitonin, estrogen, progestin, testosterone, glucagon, glucagon-like peptide (GLP-1) and its analogs, for example. The active ingredient may also be a protein, enzyme, a peptide, a polysaccharide, a nucleic acid, a cell fragment, a biologically active substance, a salt, or the like. The active agent may also be a lipid such as, but not limited to, fat-soluble vitamins (e.g., vitamins A, D, E and K), ceramides in which the fatty acid components may be one or more of the following: alpha-hydroxy 6-hydroxy-4-sphingenine, alpha-hydroxy phytosphingosine, alpha-hydroxy sphingosine, ester linked omega-hydroxy 6-hydroxy-4-sphingenine, non-hydroxy phytosphingosine, non-hydroxy sphingosine, and/or ester linked omega-hydroxysphingosine and free sterols.

One or more cannabinoids may also be delivered. The term "cannabinoid" as used herein, refers to a class of diverse chemical compounds that acts on cannabinoid receptors in cells that alter the neurotransmitter response in the brain. Ligands for these receptor proteins include the endocannabinoids (produced within the body by animals), the phytocannabinoids (found in cannabis and some other plants), and synthetic cannabinoids (not present in nature). The most notable cannabinoids are tetrahydrocannabinol (THC, the primary psychoactive compound in cannabis), cannabidiol (CBD, the non-psychoactive compound in cannabis), and their acidic forms of tetrahydrocannabinolic acid (THCA) and cannabidiolic acid (CBDA). Other notable cannabinoids are again either found in their decarboxylated forms and acidic forms, such as cannabigerol (CBG) and cannabigerolic acid (CBGA), cannabichromene (CBC) and cannabichromenic acid (CBCA). Each of these decarboxylated and acidic forms have corresponding homologs in which the propyl (3-carbon) side chain is present in place of a pentyl (5-carbon) side chain on the compound. For the four most notable cannabinoids, the corresponding decarboxylated and acidic forms are as follows: tetrahydrocannabivarin (THCV), tetrahydrodrocannabivarin carboxylic acid (THCVA), cannabidivarin (CBDV), cannabidivarin carboxylic acid (CBDVA), cannabigerovarin (CBGV), cannabigerovarin carboxylic acid (CBGVA), cannabichromevarin (CBCV), cannabichromevarin carboxylic acid (CBCVA). Other notable cannabinoids which are chemically derived products of the notable cannabinoids include cannabinol (CBN), cannabicyclol (CBL), cannabivarin (CBV). Other minor cannabinoids include cannabigerol monomethyl ether (CBGM), cannabielsoin (CBE), and cannabicitran (CBT), cannabicylolic acid (CBLA), cannabicyclovarin (CBLV), cannabidiorcol (CBD-C1), cannabigerolic acid monomethyl ester (CBGAM), cannabinodiol (CBND), cannabinol methylether (CBNM), cannabinol-C2 (CBN-C2), cannabinol-C4 (CBN-C4), cannabinolic acid (CBNA), cannabiorcol (CBN-C1), 10-ethoxy-9-hydroxy-delta-6a-tetrahydrocannabinol, 8,9-dihydroxy-delta-6a-tetrahydrocannabinol, cannabitriol, cannabitriolvarin (CBTV), delta-8-tetrahydrocannabinol (Δ8-THC), delta-8-tetrahydrocannabinol (A8-THCA), tetrahydrocannabinol-C4 (THC-C4), tetrahydrocannabinolic acid B (THCA-B), tetrahydrocannabinolic acid-C4 (THCA-C4), tetrahydrocannabiorcol (THC-C1), tetrahydrocannabiorcolic acid (THCA-C1), 10-oxo-delta-6a-tetrahydrocannabinol (OTHC), cannabichromanone (CBCF), cannabifuran (CBF), cannabiglendol, cannabiripsol (CBR), dehydrocannabifuran (DCBF), cis-tetrahydrocannabinol (cis-THC), tryhydroxy-teterahydrocannabinol (triOH-THC), cannabinerolic acid, cannabidiol monomethyl ester (CBDM), cannabidiol-C4 (CBD-C4), cannabinovarin (CBNV), (−)-(9R, 10R)-trans-cannabitriol, (+)-(9S,10S)-cannabitriol, (±)-(9R,10S/9S,10R)-cannabitriol, (−)-(9R,10R)-trans-10-O-ethyl-cannabitriol, (±)-(9R, 10R/9S,10S)-cannabitriol-C3, cannabiolic acid cannabitriol, (−)-6a,7,10a-trihydroxy-tetrahydrocannabinol, CBDA-9-OH-CBT-C5ester,(−)-cannabitetrol,5aS,6S,9R,9aR)-cannabielsoin, (5aS,6S,9R,9aR)-C3-cannabielsoin, (5aS,6S,9R,9aR)-cannabielsoic acid A, (5aS,6S,9R,9aR)-cannabielsoic acid B, (5aS,6S,9R,9aR)-C3-cannabielsoic acid B, cannabiglendol-C3, (−)-Δ7-trans-(1R,3R,6R)-isotetrahydrocannabinol, (±)-Δ7-1,2-cis-(1R,3R,6S/1S,3S,6R)-isotetrahydrocannabivarin, (−)-Δ7-trans-(1R,3R,6R)-isotetrahydrocannabivarin, cannabichromanone-C3, cannabicoumaronone, and 3,4,5,6-tetrahydroxy-alpha-2-trimethyl-9-n-propyl-2,6-methano-2H-1-benzoxocin-5-methanol. Other cannabinoids from nature not derived from cannabis plants include alykylamides, catechins, beta-caryophyllene, anandamide, 7,10,13,16-docosatetraenolyethanolamide, homo-γ-linolenoylethanolamine, N-acylethanolamines, 2-arachidonoylglycerol, 2-arachidonyl glyceryl ether, N-arachidonoyl dopamine (NADA), virodhamine (OAE), and lysophosphatidylinositol (LPI). Notable cannabinoids which are synthetic and thus not derived from nature include marinol, cesamet, SR141716, JWH-018, JWH-073, CP-55940, HU-210, HE-331, SR144528, WIN 55,212-2, JWH-133, nantrodolum, and AM-2201.

One or more than one of the foregoing active ingredients, may be combined together in a single pharmaceutical formulation or administered serially. The active ingredients can be included, for example, in a physiologically acceptable carrier. As used herein, the term "physiologically acceptable carrier" refers to a diluent (i.e., a substance used to dilute something), adjuvant, excipient, or the like vehicle in which a therapeutic agent is administered. Such carriers can include alcohol, starch, glucose, lactose, sucrose, gelatin, malt, rice, flour, chalk, silica gel, sodium stearate, glycerol monostearate, talc, sodium chloride, dried skim milk, or any compound found in the *Handbook of Pharmaceutical Excipients* (4$^{th}$ edition, Pharmaceutical Press) and the like. A minor amount of wetting or emulsifying agents, or pH buffering agents such as acetates, citrates, or phosphates may also be present. Also, antibacterial agents such as methyl parabens; antioxidants such as ascorbic acid or sodium metabisulfite; chelating agents such as ethylenediaminetetraacetic acid (EDTA); and agents for the adjustment of tonicity such as sodium chloride or dextrose may be present. Preservatives commonly known to those of skill in the art may also be present.

The active ingredients can be included in the formulation for use in the device described herein in a therapeutically effective amount. As used herein, the term "therapeutically effective amount" refers to those amounts that, when administered to a particular subject in view of the nature and severity of that subject's disease or condition, will have a desired therapeutic effect, (e.g., an amount which will cure, prevent, inhibit, or at least partially arrest or partially prevent a target disease or condition).

In certain embodiments, the device may be used to deliver naloxone (e.g., naloxone hydrochloride).

Plant-based resins from tree exudates are suitable and commonly used in the medical arts for enhancing adherence of surgical bandages. Tincture of benzoin (TOB) is readily available through numerous commercial sources including drug stores and suppliers of surgical goods. TOB is an oral mucosal protectant that is FDA and ADA approved for use in the mouth, is on the GRAS list as a food additive, and is a well-accepted treatment for intraoral stomatitis.

To this end, in one test, naloxone hydrochloride is combined with Tincture of Benzoin (TOB) at 4 and 40 mg/mL. TOB contains 17-24% *Styrax benzoin* resin in 79-83% alcohol. After it is applied to the mucosa by swab, the alcohol evaporates and the remaining benzoin resin that adheres and maintains drug contact to the oral mucosa for up to 2 hours. The adhesiveness of benzoin resin to the buccal mucosa maintains drug contact and concentration gradient to facilitate immediate naloxone permeation and systemic absorption allowing sustained release of naloxone.

In addition, the device described herein can be used for the buccal delivery of a vaccine composition to a patient. A vaccine composition can include an antigen dispersed within a vehicle, such as an amorphous solid. As used herein, the term "antigen" means a substance that induces a specific immune response in a host animal. The antigen may comprise a whole organism, killed, attenuated or live (including killed, attenuated or inactivated bacteria, viruses, fungi, parasites, prions or other microbes); a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternatively, the antigen can include a toxin or antitoxin.

An amorphous solid suitable for use as a vehicle should be dissolvable upon contact with an aqueous liquid, such as a saliva. In some embodiments, amorphous solids suitable for use in the present disclosure may be formed from any sugar, sugar derivative or combination of sugars/derivatives. The sugar and/or derivative is preferably prepared as a liquid solution at a concentration that allows it to flow freely when poured but also forms an amorphous phase at ambient temperatures on a physical surface that facilitates this process, such as aluminum or Teflon. Examples of suitable sugars may include, for example, glucose, dextrose, fructose, lactose, maltose, xylose, sucrose, corn sugar syrup, sorbitol, hexitol, maltilol, xylitol, mannitol, melezitose, raffinose, and combinations thereof. In some embodiments, an amorphous solid suitable for use in the present disclosure may have a thickness of about 0.05 millimeters to about 5 millimeters.

In addition, in some embodiments, certain sugars may also function as a binder which may provide bulk to pharmaceutical preparations that contain small quantities of very potent medications for ease of handling/administration. They may also hold components together or promote binding to surfaces (like the film backing) to ease drug delivery and handling.

Optionally, the vaccine compositions may comprise a water-soluble polymer including, but not limited to, carboxymethyl cellulose, carboxyvinyl polymers, high amylose starch, hydroxyethyl cellulose, hydroxypropyl cellulose, hydroxypropyl methylcellulose, methylmethacrylate copolymers, polyacrylic acid, polyvinyl alcohol, polyvinyl pyrrolidone, pullulan, sodium alginate, poly(lactic-co-glycolic acid), poly(ethylene) oxide, poly(hydroxyalkanoate) and a combination thereof.

Furthermore, in some embodiments, the vaccine compositions described herein may further comprise one or more oils, polyalcohols, surfactants, permeability enhancers, and/or edible organic acids. Examples of suitable oils may include, for example, eucalyptol, menthol, vacrol, thymol, methyl salicylate, verbenone, eugenol, gerianol and combinations thereof. Examples of suitable polyalcohols may include, for example, glycerol, polyethylene glycol, propylene glycol, and combinations thereof. Examples of suitable edible organic acids may include, but are not limited to, citric acid, malic acid, tartaric acid, fumaric acid, phosphoric acid, oxalic acid, ascorbic acid and combinations thereof. Examples of suitable surfactants may include, but are not limited to, difunctional block copolymer surfactants terminating in primary hydroxyl groups, such as Pluronic® F68 commercially available from BASF, poly(ethylene) glycol 3000, dodecyl-β-D-maltopyranoside, disodium PEG-4 cocamido MIPA-sulfosuccinate ("DMPS"), and the like.

A vaccine composition for use in the systems described herein further comprises an antigen. Antigens suitable for use in the present disclosure may include any antigen for which cellular and/or humoral immune responses are desired, including antigens derived from viral, bacterial, fungal and parasitic pathogens and prions that may induce antibodies, T-cell helper epitopes and T-cell cytotoxic epitopes. Such antigens include, for example, those encoded by human and animal viruses and can correspond to either structural or non-structural proteins. Furthermore, the present disclosure contemplates vaccines made using antigens derived from any of the antigen sources discussed below and those that use these sources as potential delivery devices or vectors.

Antigens useful in the present disclosure may include those derived from viruses including, but not limited to, those from the family Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E, OC43, NL63, HKU1, MERS-CoV, SARS-CoV, SARS-CoV-2), Deltavirus (e.g., Hepatitis delta virus), Filoviridae (e.g., Marburg virus, Ebola virus), Flaviviridae (e.g., Yellow fever virus group, Hepatitis C virus), Hepadnaviridae (e.g., Hepatitis B virus), Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C), Papovaviridae (e.g., Papillomavirus), Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus, Cardiovirus such as Encephalomyocarditis virus, Aphthovirus such as Foot-and-mouth disease virus O, Coxsackie virus), Poxyiridae (e.g., Orthopoxvirus such as Variola virus or monkey poxvirus), Reoviridae (e.g., Rotavirus such as Groups A-F rotaviruses), Retroviridae (Primate lentivirus group such as human immunodeficiency virus 1 and 2), Rhabdoviridae (e.g., rabies virus), Togaviridae (e.g., Rubivirus such as Rubella virus), Human T-cell leukemia virus, Murine leukemia virus, Vesicular stomatitis virus, Wart virus, Blue tongue virus, Sendai virus, Feline leukemia virus, Simian virus 40, Mouse mammary tumor virus, Dengue virus, HIV-1 and HIV-2, West Nile, H1N1, SARS, 1918 Influenza, Tick-borne encephalitis virus complex (Absettarov, Hanzalova, Hypr), Russian Spring-Summer encephalitis virus, Congo-Crimean Hemorrhagic Fever virus, Junin Virus, Kumlinge Virus, Marburg Virus, Machupo Virus, Kyasanur Forest Disease Virus, Lassa Virus, Omsk Hemorrhagic Fever Virus, FIV, SIV, Herpes simplex 1 and 2, Herpes Zoster, Human parvovirus (B19), Respiratory syncytial virus, Pox viruses (all types and serotypes), Coltivirus, Reoviruses-all types, and/or Rubivirus (rubella).

Antigens useful in the devices and methods described herein can include those derived from bacteria including, but not limited to, *Streptococcus agalactiae*, *Legionella pneumophilia*, *Streptococcus pyogenes*, *Escherichia coli*, *Neisseria gonorrhosae*, *Neisseria meningitidis*, *Pneumococcus*, *Hemophilis influenzae* B, *Treponema pallidum*, Lyme disease spirochetes, *Pseudomonas aeruginosa*, *Mycobacterium leprae*, *Brucella abortus*, *Mycobacterium tuberculosis*, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japanicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M hyorhinis*, *M. orale*, *M. arginini*, *Acholeplasma laidlawii*, *M. salivarium*, *M. pneumoniae*, *Candida albicans*, *Cryptococcus neoformans*, *Histoplasma capsulatum*, *Coccidioides immitis*, *Blastomyces dermatitidis*, *Aspergillus fumigatus*, *Penicillium marneffei*, *Bacillus anthracis*, *Bartonella*, *Bordetella pertussis*, *Brucella*—all serotypes, *Chlamydia trachomatis*, *Chlamydia pneumoniae*, *Clostridium botulinum*-anything from *clostridium* serotypes, *Haemophilus influenzae*, *Helicobacter pylori*, *Klebsiella*—all serotypes, *Legionella*—all serotypes, *Listeria*, *Mycobacterium*—all serotypes, *Mycoplasma*—human and animal serotypes, *Rickettsia*—all serotypes, *Shigella*—all serotypes, *Staphylococcus aureus*, *Streptococcus*—*S. pneumoniae*, *S. pyogenes*, *Vibrio cholera*, *Yersinia enterocolitica*, and/or *Yersinia pestis*.

Antigens useful in the devices and methods described herein can include those derived from parasites including, but not limited to, *Ancylostoma* human hookworms, *Leishmania*—all strains, *Microsporidium*, Necator human hookworms, *Onchocerca* filarial worms, *Plasmodium*—all human strains and simian species, *Toxoplasma*—all strains, *Trypanosoma*—all serotypes, and/or *Wuchereria bancrofti* filarial worms.

The vaccine compositions can be prepared using techniques known to those of ordinary skill in the art. For example, a vaccine composition of the present disclosure may be made by contacting an amorphous solid with an antigen, or optionally, mixing an antigen with one or more excipients (surfactants, sugars, starches, etc.) and contacting the amorphous solid with the mixture so as to dispose the antigen within the amorphous solid. In some embodiments, the mixture is then allowed to dry, which is then ready for administration.

The amount of antigen that may be used in a vaccine composition as described herein can vary greatly depending upon the type of antigen used, the formulation used to prepare the vaccine composition, the size of the amorphous solid, the solubility of the antigen, and the like. A person of ordinary skill in the art, with the benefit of this disclosure, will be able to determine a suitable amount of antigen to include in a vaccine composition. In one embodiment, a vaccine composition may comprise about $1 \times 10^6$ to about $1 \times 10^{13}$ virus particles for a virus-based vaccine or about $1 \times 10^3$ to about $1 \times 10^{13}$ colony forming units for a bacteria-based vaccine.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention. During the studies described in the following examples, conventional procedures were followed, unless otherwise stated. Some of the procedures are described below for illustrative purposes.

EXAMPLES

Figure 8:
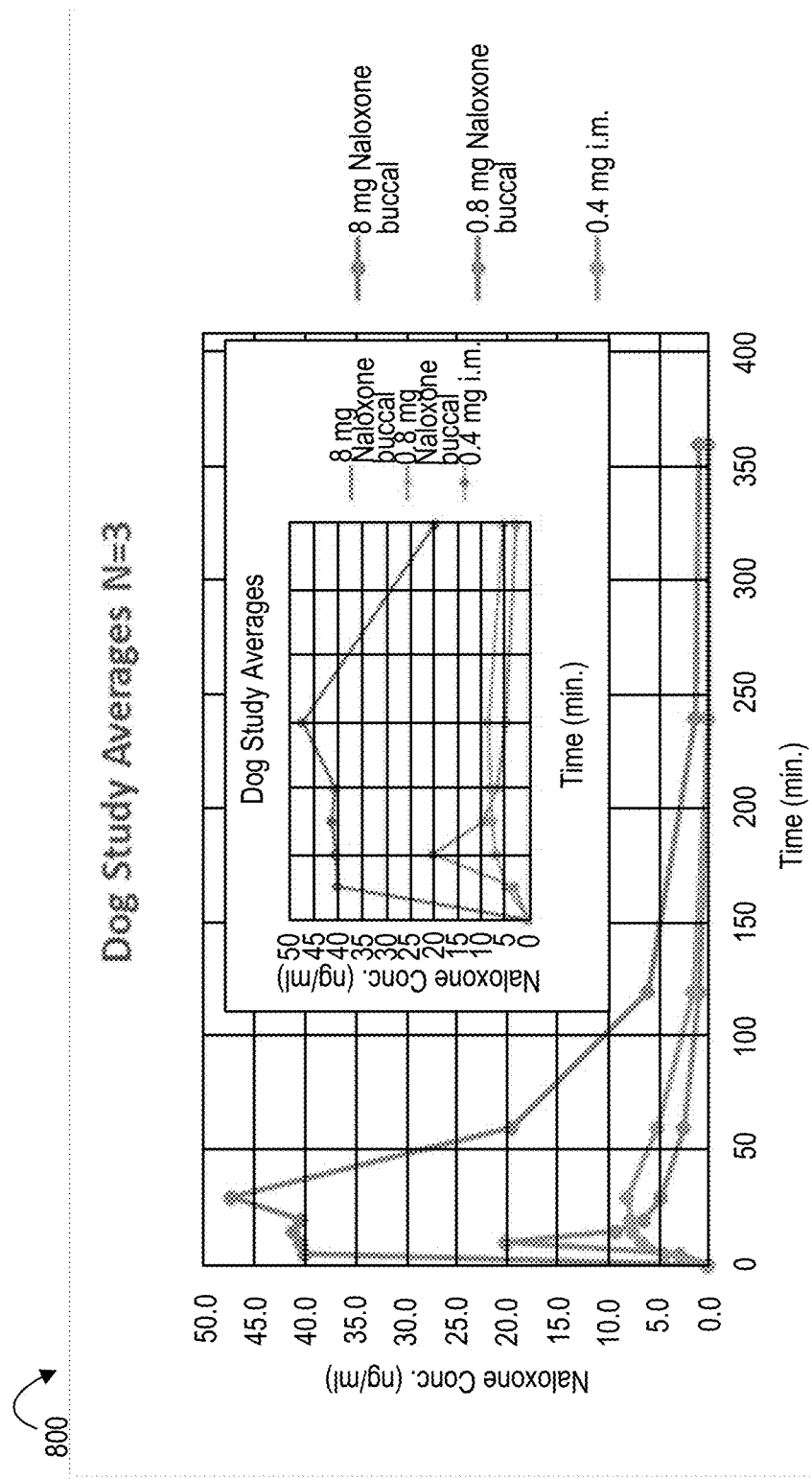
FIG. 8 is a graph showing naloxone concentration versus time for various dosages and delivery methods in dogs, according to some aspects of the present disclosure.
Figure 9:
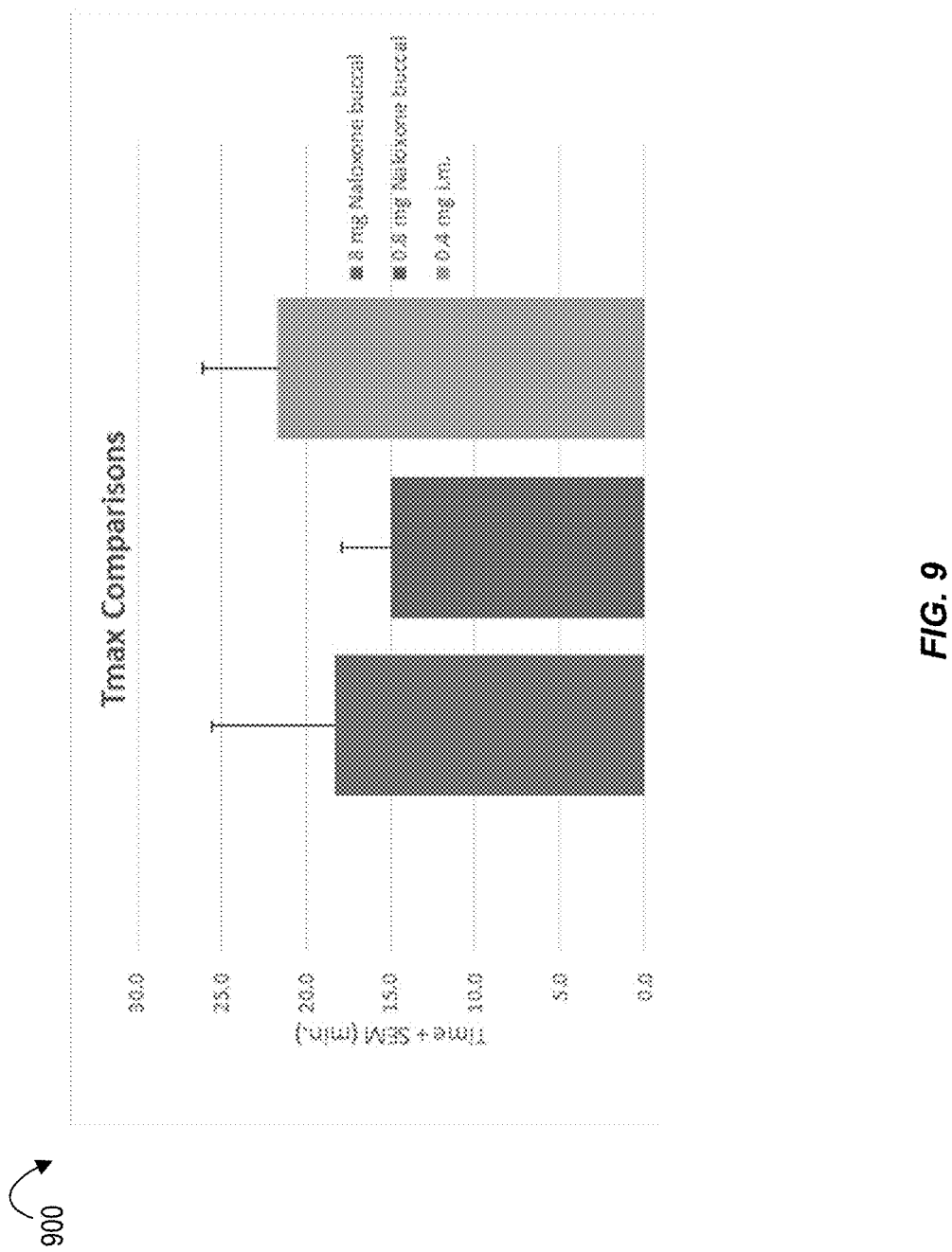
FIG. 9 is a graph showing a Tmax comparison for various concentrations of naloxone using different delivery methods in dogs, according to some aspects of the present disclosure.
Figure 10:
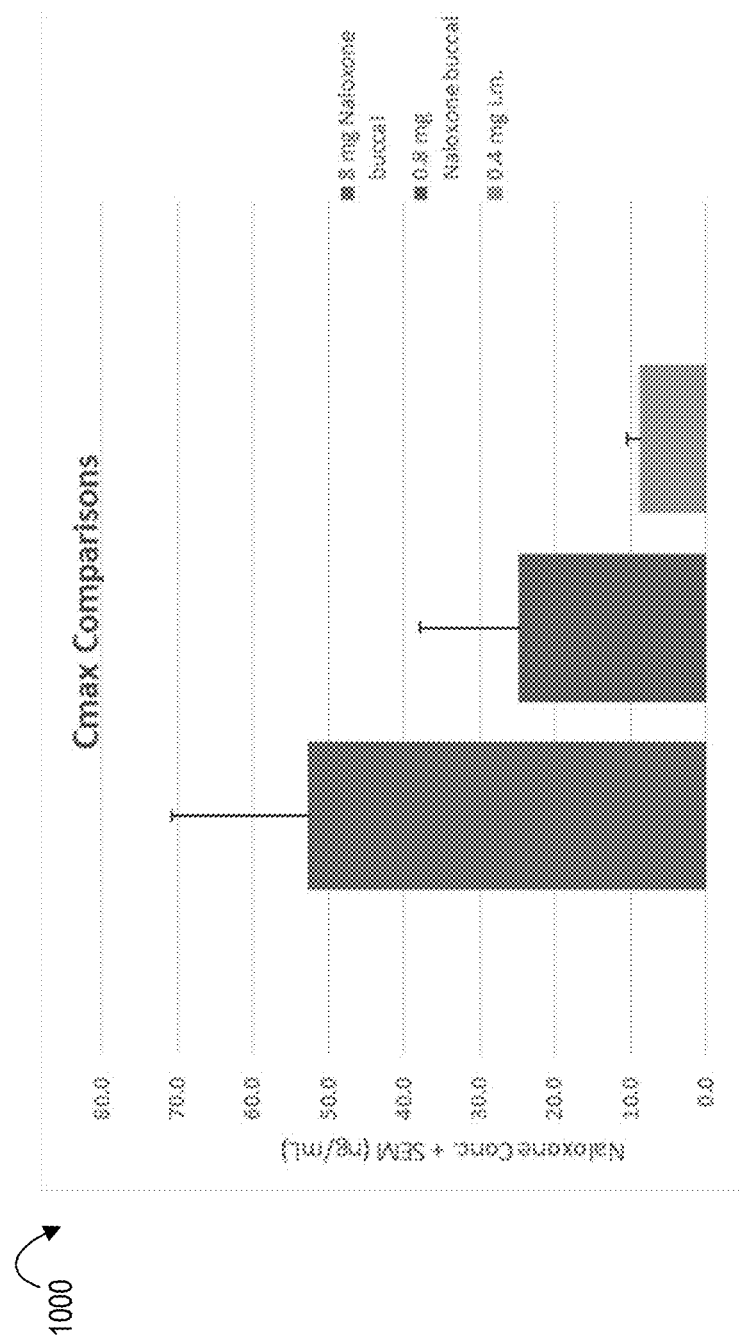
FIG. 10 is a graph showing a Cmax comparison for various concentrations of naloxone using different delivery methods in dogs, according to some aspects of the present disclosure.

FIG. 8 is a graph 800 showing the naloxone concentration versus time for various dosages and delivery methods in dogs. FIG. 9 is a graph 900 showing the Tmax comparisons for various concentrations of naloxone using different delivery methods in dogs. FIG. 10 is a graph 1000 showing the Cmax comparisons for various concentrations of naloxone using different delivery methods in dogs. FIGS. 8-10 are described by the Clinical Examples below.

Example 1: In Vivo Studies in Dogs

A proof-of-concept transbuccal pharmacokinetic (PK) delivery study was completed in predictive dog models demonstrating comparable blood levels to benchmark intramuscular injection. The results are shown in FIGS. 8-10. In particular, the combination of naloxone HCl with TOB applied to the buccal surface demonstrated rapid systemic absorption of naloxone with sustained delivery component.

The canine oral cavity mucosal surface is less keratinized than rodents and is the standard animal method for evaluating transbuccal systemic delivery of drugs in humans. This preliminary preclinical dog PK study demonstrated buccal delivery achieves equivalent blood levels to the intramuscular (IM) route.

In one example, a preliminary formulation of naloxone hydrochloride in tincture of benzoin at two dose strengths (4.0 mg/mL and 40.0 mg/mL). This formulation was applied by buccal swabbing in a three way crossover canine PK study and compared to a standard IM injection control (0.4 mg/ml). Buccal administration showed rapid appearance of naloxone in the blood, sooner and at higher levels than IM.

An exemplary composition for the drug product formulation is provided in Table 1. The composition can also include one or more additives (e.g., stabilizing additives).

TABLE 1

| Drug Product Components/Composition | | | | | |
|---|---|---|---|---|---|
| | 4 mg/mL Presentation | | 40 mg/mL Presentation | | |
| Ingredient | mg/device | mg/mL | mg/device | mg/mL | Function |
| Naloxone Hydrochloride USP | | 4 | | 40 | Active ingredient |
| Tincture of Benzoin: | | | | % | Bioadhesive |
| a) solids (resin) | | | | 17 | |
| b) ethanol | | | | 83 | |

Example 2: Exemplary Clinical Results

The clinical program is designed to show that the device reliably delivers naloxone to the bloodstream and to show bioavailability relative to approved standard of care (naloxone). Additionally, information is obtained from the clinical subjects as part of the human factor studies to show that the label and device are easy to understand and used correctly by untrained users. The proposed clinical program includes the following trials:

Initial Human PK trial of Buccal Administration of Naloxone in Bio-adhesive Formulation In this study 30 healthy volunteers participate in a 3 way crossover of naloxone formulation pipetted onto a swab and applied buccally compared to standard IM dosing. Each subject receives two different doses of buccal formulation and an IM dose once separated by a one week washout period. Full PK are measured as well as determining bioavailability relative to IM dosing A Single-Arm Open Label Pharmacokinetic Study in Healthy Volunteers to Test Reliability and Variability of NarStat™.

In this study, 50 healthy volunteers receive a single dose of NarStat™ and their PK parameters are evaluated through naloxone levels in blood at 2.5, 5, 10, 15, 20, 30, 45 and 60 minutes immediately after drug administration. The primary efficacy end point is determined by calculating the standard deviation of each time point. Additionally, $C_{max}$, $T_{max}$, and AUC are reported as secondary end points. The term "$C_{max}$" refers to the maximum (i.e., peak) serum concentration that a drug achieves in a specified test area of the body after the drug has been administrated and before the administration of a second dose. $C_{max}$ is the opposite of $C_{min}$, which is the minimum (i.e., trough) concentration that a drug achieves after dosing. The related pharmacokinetic parameter $T_{max}$ is the time at which the $C_{max}$ is observed. The "area under the curve" or AUC ranges from zero to infinity and represents the total drug exposure over time. Assuming linear pharmacodynamics with elimination rate constant K, the AUC is proportional to the total amount of drug absorbed by the body.

A Bioequivalence 4 Way Crossover Study of 2 Doses of NarStat™ vs IM Naloxone.

In this pivotal study, 30 healthy volunteers are assigned to each of the following four groups, one week apart, at the beginning of each week: (1) NarStat™ standard dose; (2) NarStat™ high dose; (3) naloxone IM standard dose; and (4) Narcan standard dose.

Naloxone levels in blood at 5, 10, 15, 20, 30, 45 and 60 minutes immediately after drug administration are measured. Primary end points are determined by comparing blood levels of NarStat™ versus IM Naloxone. As secondary endpoints, NarStat™ PK parameters are compared to those of Narcan.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the present invention as defined in the following claims.

What is claimed is:
1. A drug product delivery device comprising:
   a housing;
   a plunger comprising a molded component with a cover film that forms a series of fluidic channels on a first elongated surface of the plunger;
   a foil drug reservoir cap bonded to a second elongated surface of the plunger, wherein the foil drug reservoir cap creates a fluid storage chamber disposed between the foil drug reservoir cap and the second elongated surface of the plunger;
   a frangible seal component attached to the second elongated surface of the plunger, wherein the frangible seal component blocks a fluid from moving from the fluid storage chamber into the series of fluidic channels; and
   an applicator positioned at a tip of the plunger and exposed to the series of fluidic channels, wherein actuation of the plunger pushes the plunger into the housing to rupture of the frangible seal component, which causes the fluid to exit the fluid storage chamber and pass through the ruptured frangible seal component into the series of fluidic channels and into contact with the applicator.

2. The drug product delivery device of claim 1, further comprising:
   a drug storage chamber arranged on the plunger between the frangible seal component and the series of fluidic channels, the drug storage chamber storing a dry drug; and
   wherein activation of the plunger causes the frangible seal component to rupture and the fluid to exit the fluid storage chamber and pass through the ruptured frangible seal component and into the drug storage chamber for mixture with the dry drug before the fluid and dry drug mixture enters into the series of fluidic channels and into contact with the applicator.

3. The drug product delivery device of claim 2, wherein the fluid comprises a carrier fluid and a dry drug comprises a small molecule drug.

4. The drug product delivery device of claim 1, wherein the applicator is a flock swab.

5. The drug product delivery device of claim 4, wherein the flock swab is a sterile flock swab.

6. The drug product delivery device of claim 1, wherein the frangible seal component comprises an overmolded rigid polypropylene part with a thermoplastic elastomer (TPE) gasket.

7. The drug product delivery device of claim 1, wherein the housing comprises a rigid plastic housing.

8. The drug product delivery device of claim 7, wherein the rigid plastic housing comprises a plurality of molded parts attached together.

9. The drug product delivery device of claim 1, wherein the fluid comprises a small molecule drug.

10. The drug product delivery device of claim 1, wherein the fluid comprises a vaccine.

11. A method of delivering a drug on a swab, the method comprising:
   actuating a plunger of a drug product delivery device to push the plunger into a housing of the drug product delivery device, wherein the drug product delivery device comprises:
   the plunger, wherein the plunger comprises a molded component with a cover film that forms a series of fluidic channels on a first elongated surface of the plunger,
   a foil drug reservoir cap bonded to a second elongated surface of the plunger to create a fluid storage chamber disposed between the foil drug reservoir cap and the second elongated surface of the plunger, a frangible seal component attached to the second elongated surface of the plunger to block a fluid comprising a pharmaceutically active ingredient from moving from the fluid storage chamber into the series of fluidic channels, and an applicator positioned at a tip of the plunger and exposed to the series of fluidic channels, wherein actuating the plunger causes the frangible seal component to rupture, and the fluid to exit the fluid storage chamber and pass through the ruptured frangible seal component into the series of fluidic channels and into contact with the applicator; and delivering, using the applicator, the drug onto a buccal surface.

12. The method of claim 11, wherein the pharmaceutically active ingredient comprises a small molecule drug.

13. The method of claim 11, wherein the pharmaceutically active ingredient comprises a vaccine composition.

14. The method of claim 11, the drug product delivery device further comprises:

a drug storage chamber arranged on the plunger between the frangible seal component and the series of fluidic channels, the drug storage chamber storing a dry drug; and wherein activation of the plunger causes the frangible seal component to rupture and the fluid to exit the fluid storage chamber and pass through the ruptured frangible seal component and into the drug storage chamber for mixture with the dry drug before the fluid and dry drug mixture enters into the series of fluidic channels and into contact with the applicator.

15. The method of claim 11, wherein the applicator is a flock swab.

16. The method of claim 11, wherein the applicator is a sterile flock swab.

17. The method of claim 11, wherein the frangible seal component comprises an overmolded rigid polypropylene part with a thermoplastic elastomer (TPE) gasket.

18. The method of claim 11, wherein the housing comprises a rigid plastic housing.

19. The method of claim 18, wherein the rigid plastic housing comprises a plurality of molded parts attached together.

20. The method of claim 11, wherein the fluid comprises a carrier fluid and a dry drug comprises a small molecule drug.

* * * * *